(12) United States Patent
Manna et al.

(10) Patent No.: US 6,736,814 B2
(45) Date of Patent: *May 18, 2004

(54) ULTRASONIC MEDICAL TREATMENT DEVICE FOR BIPOLAR RF CAUTERIZATION AND RELATED METHOD

(75) Inventors: Ronald R. Manna, Valley Stream, NY (US); Dan Voic, Clifton, NJ (US); Theodore A. D. Novak, King Park, NY (US); Scott Isola, Deer Park, NY (US); Alexander L. Darian, Huntington Station, NY (US)

(73) Assignee: Misonix, Incorporated, Farmingdale, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/086,508

(22) Filed: Feb. 28, 2002

(65) Prior Publication Data

US 2003/0163130 A1 Aug. 28, 2003

(51) Int. Cl.[7] .................................................. A61B 18/12
(52) U.S. Cl. ............................. 606/50; 606/49; 606/50; 606/51; 606/41
(58) Field of Search .............................. 606/40, 41, 45, 606/48, 49, 50, 51, 52; 604/21, 22; 601/2

(56) References Cited

U.S. PATENT DOCUMENTS

| | | | |
|---|---|---|---|
| 4,750,902 A | | 6/1988 | Wuchinich et al. |
| 4,931,047 A | * | 6/1990 | Broadwin et al. ............. 604/22 |
| 5,013,312 A | * | 5/1991 | Parins et al. ................... 606/37 |
| 5,630,837 A | * | 5/1997 | Crowley ........................... 601/2 |
| 5,776,092 A | * | 7/1998 | Farin et al. .................... 604/22 |
| 6,235,024 B1 | * | 5/2001 | Tu ................................. 606/41 |
| 6,394,973 B1 | * | 5/2002 | Cucin ............................ 604/22 |
| 6,508,765 B2 | * | 1/2003 | Suorsa ......................... 600/439 |

FOREIGN PATENT DOCUMENTS

WO    WO 87/06116    10/1987

* cited by examiner

Primary Examiner—Roy D. Gibson
Assistant Examiner—Aaron Roane
(74) Attorney, Agent, or Firm—R. Neil Sudol; Henry D. Coleman; William J. Sapone

(57) ABSTRACT

An ultrasonic medical treatment device has a casing, an elongate probe, a transducer assembly, a sheath and a plurality of electrode members. The probe is mounted to and extends from the casing and has an axis and a free end serving as an operative tip. The transducer assembly is mounted to the casing and is operatively connected to the probe for generating vibrations of at least one ultrasonic frequency in the probe. The sheath surrounds the probe. The electrode members are connectable to an RF voltage source and are mounted at least indirectly to the casing so as to permit relative motion between the electrode members and the probe.

28 Claims, 6 Drawing Sheets

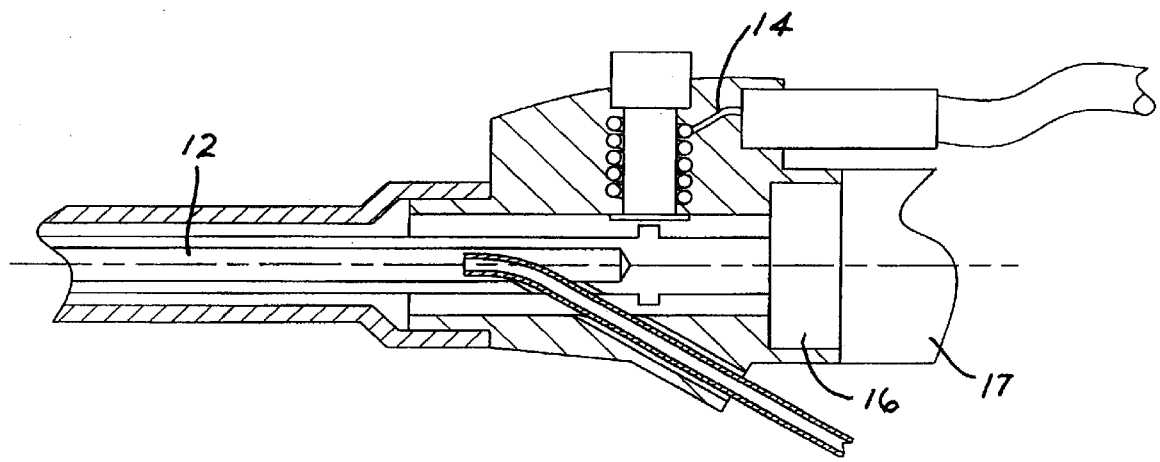
PRIOR ART
FIG. 1A
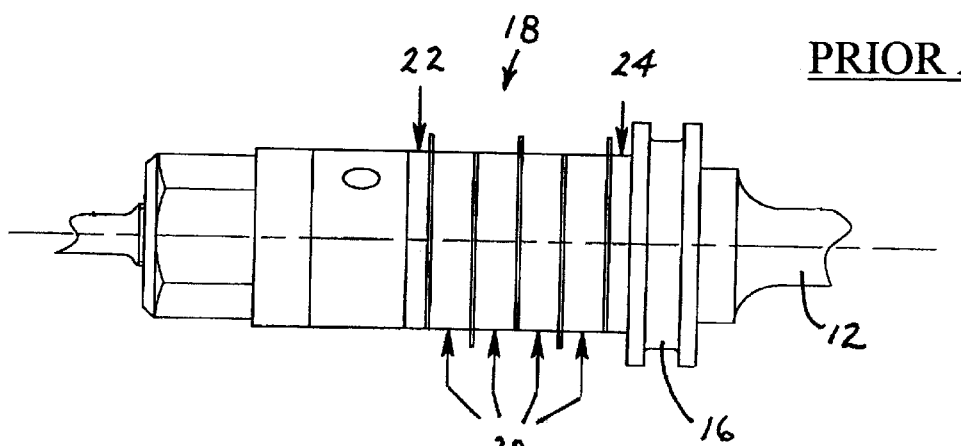
PRIOR ART
FIG. 1B

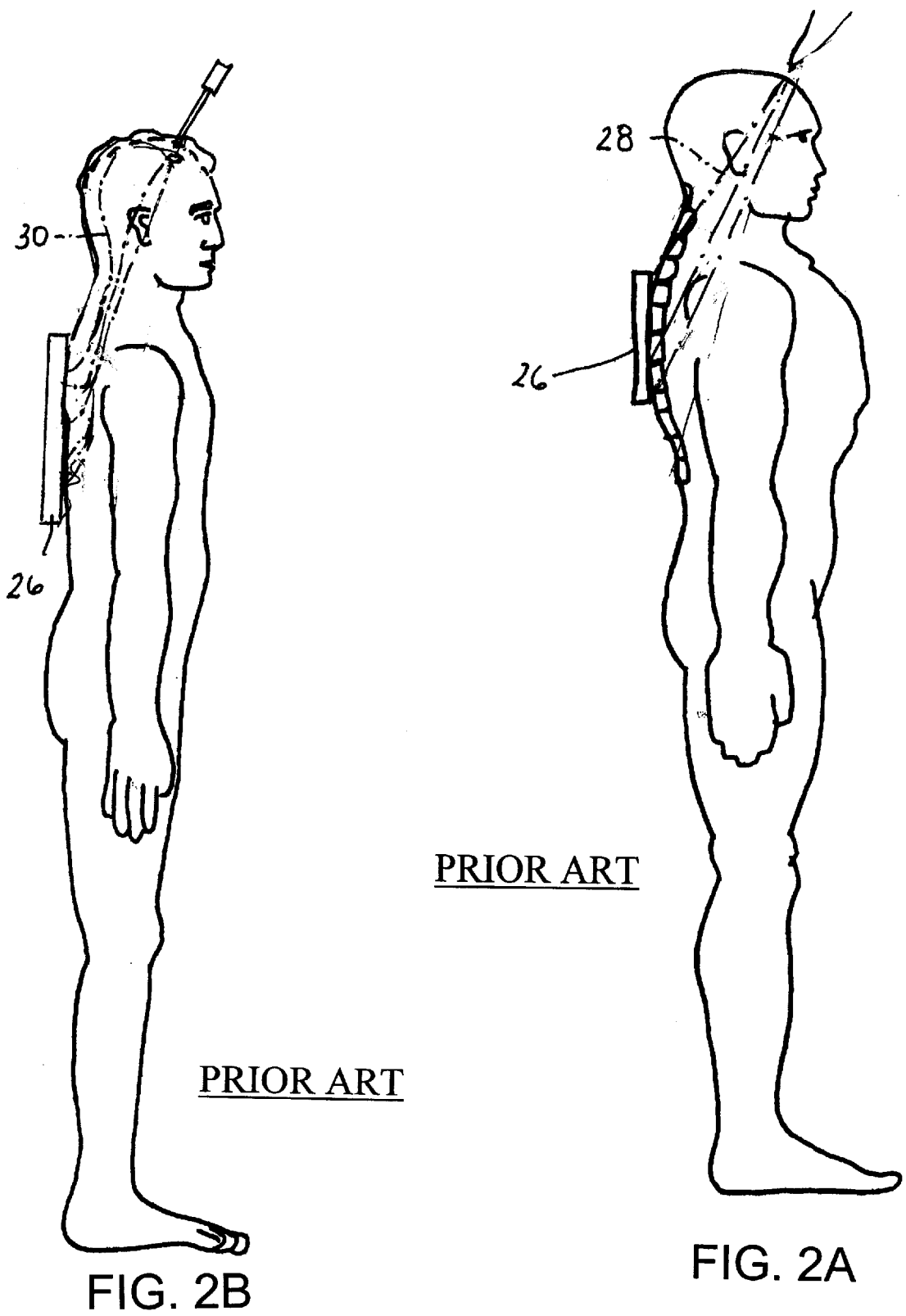
PRIOR ART
FIG. 2B
PRIOR ART
FIG. 2A

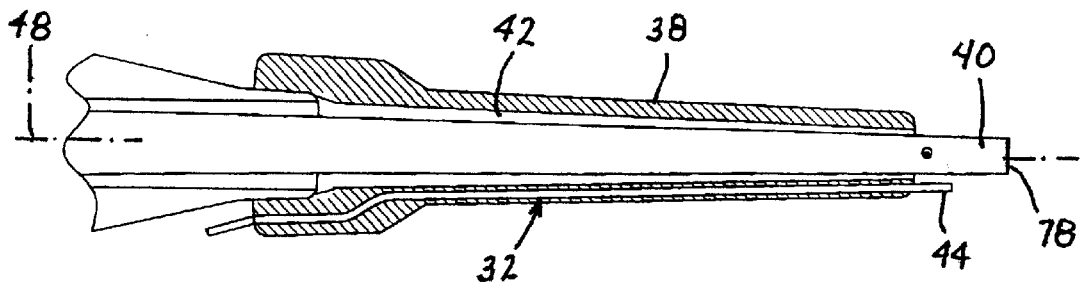
FIG. 3A
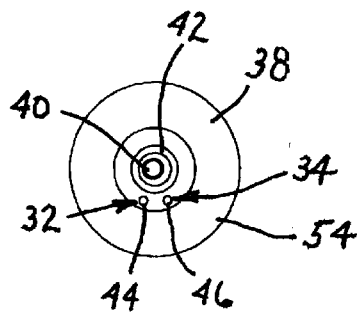
FIG. 3B
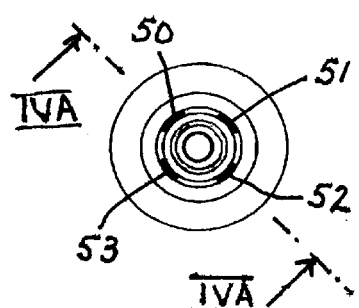
FIG. 4B
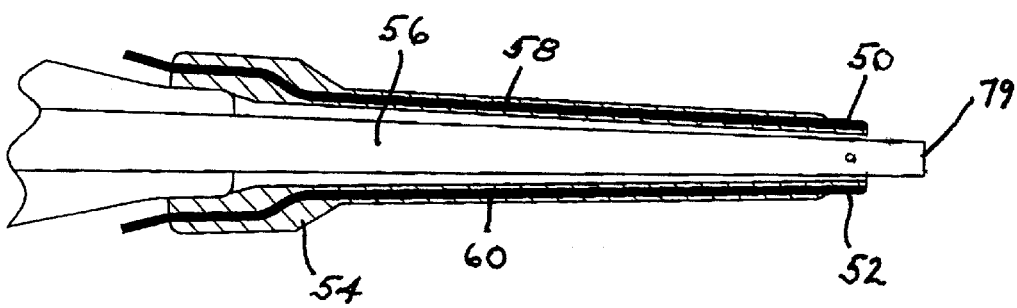
FIG. 4A

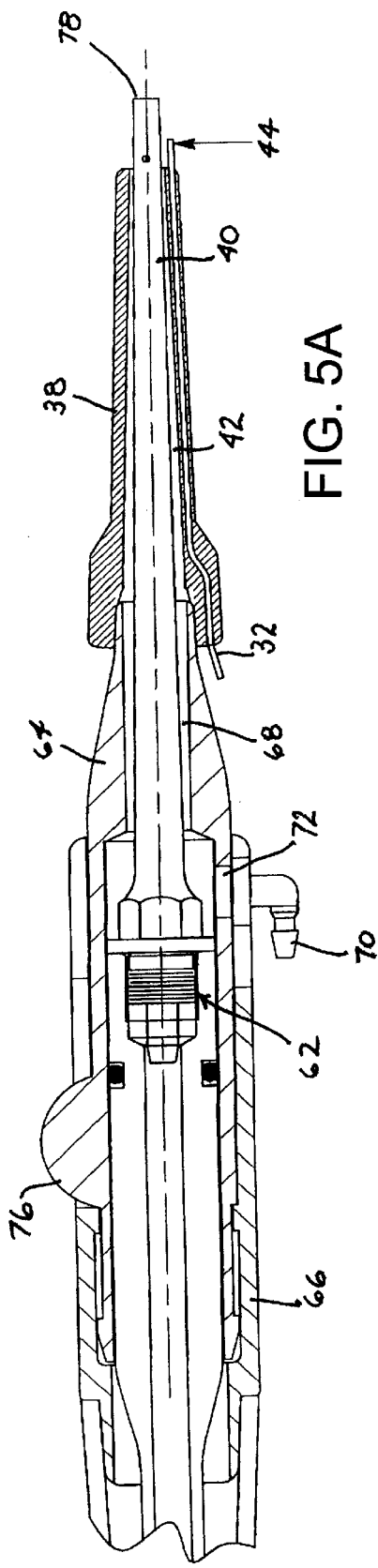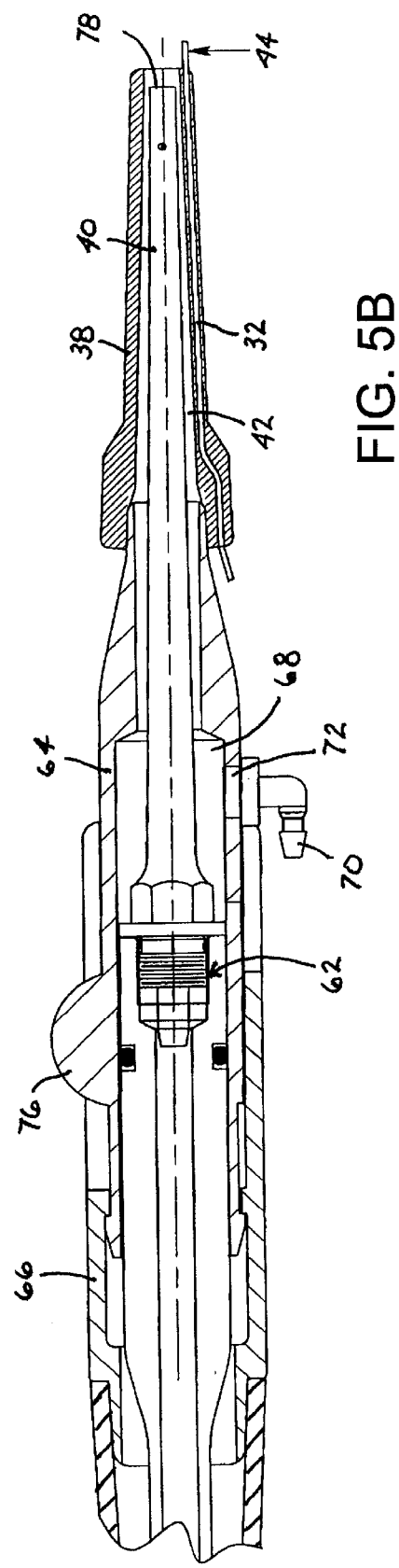
FIG. 5A
FIG. 5B

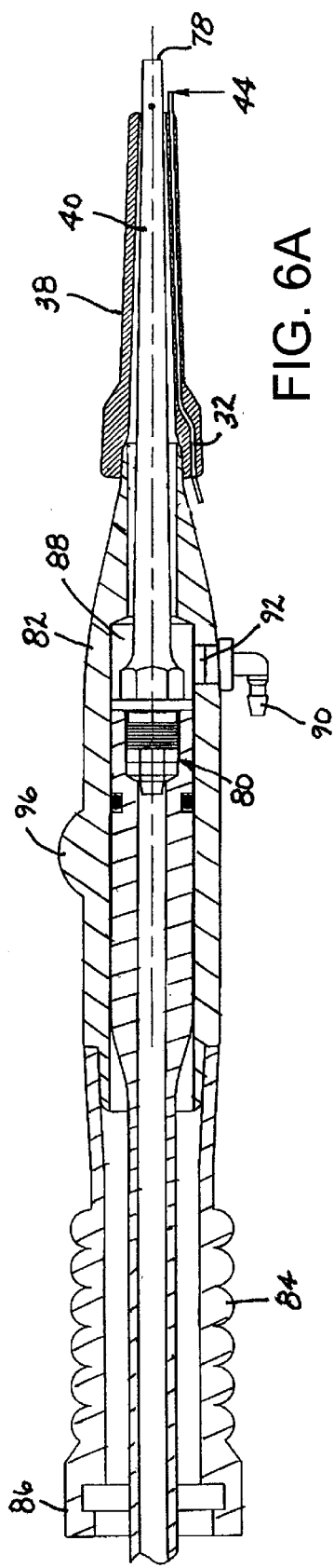
FIG. 6A
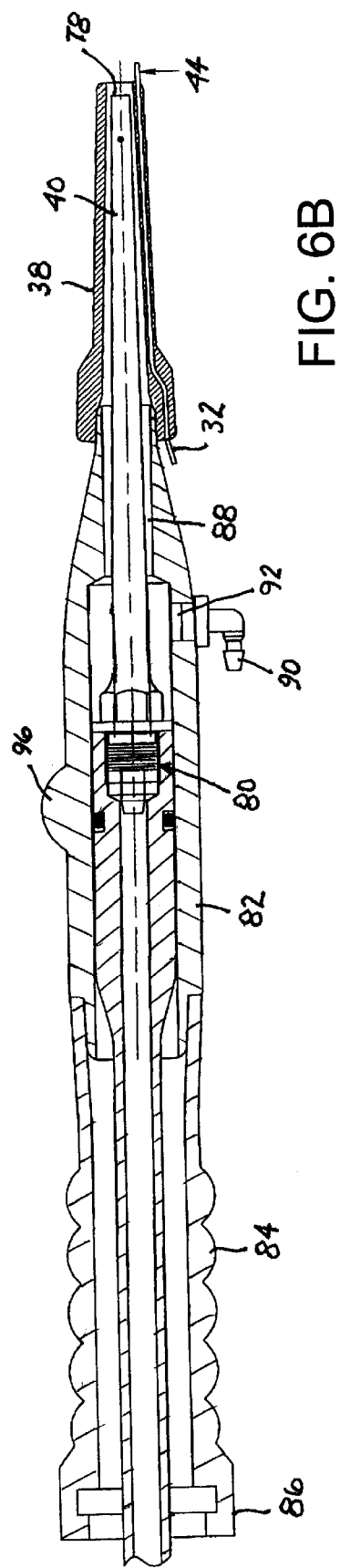
FIG. 6B

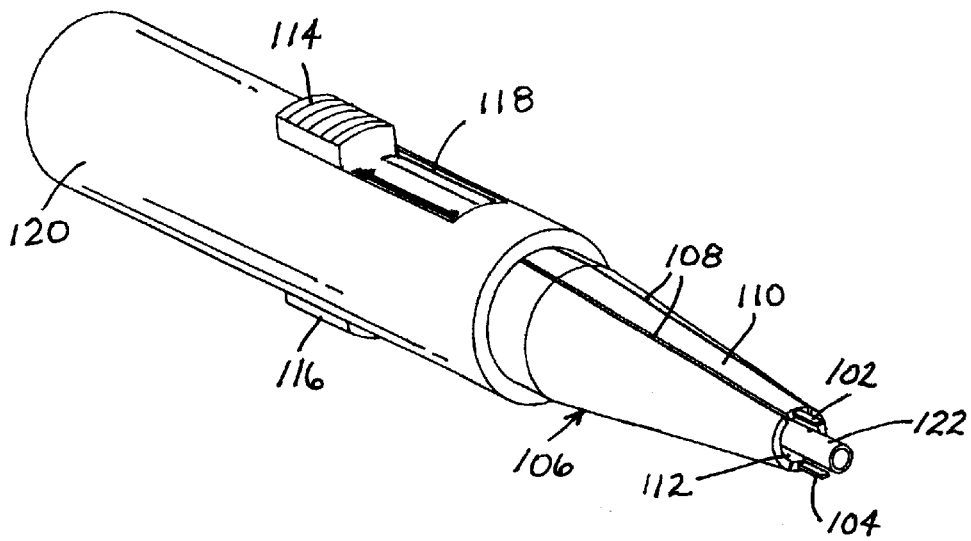
FIG. 7A
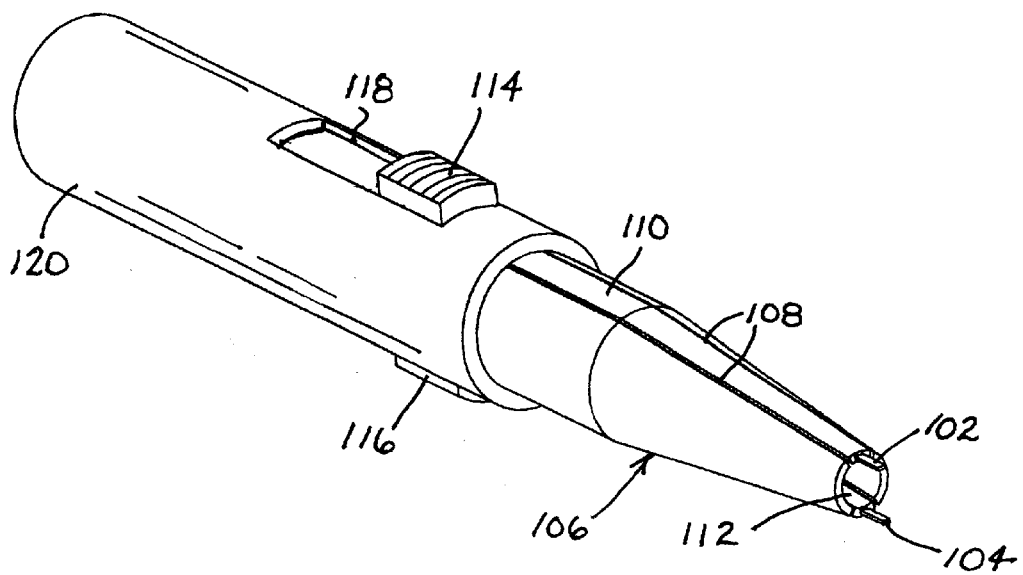
FIG. 7B

ULTRASONIC MEDICAL TREATMENT DEVICE FOR BIPOLAR RF CAUTERIZATION AND RELATED METHOD

FIELD OF THE INVENTION

This invention relates to a medical device and more specifically to an ultrasonic tissue ablation instrument. Even more specifically, this invention relates to an ultrasonic medical treatment device with electrocautery. This invention also relates to an associated medical treatment method.

BACKGROUND OF THE INVENTION

Many diseases of the brain and spine require surgery to provide the patient with relief. These could include cancer, non-malignant lesions and trauma induced by accidents or physical attack. As a procedure, neurosurgery has been practiced for several millennia. Archeologists have discovered evidence of sophisticated cranial surgery in relics and skulls dating back to Roman times. The tools found have been shown to be remarkably similar to today's designs. Of course, modern science has substantially improved upon the techniques and results obtained in those days.

One of the biggest steps forward occurred approximately 30 years ago with the invention and marketing of the ultrasonic surgical aspirator. This device utilizes a hollow probe or tool that vibrates at frequencies at or above 20 kc with tip amplitudes of up to 300 microns. When the vibrating tip is placed against viable or diseased tissue, the moving tip ablates the cells and causes them to fragment or otherwise emulsify in the irrigation fluid that is being added simultaneously. The emulsified fluid is then aspirated through the hollow probe and deposited in a canister for histological examination or disposal.

The advantage of excising tissue with this device is that the surgeon can remove the lesion in layers almost 5 cells thick. By slowly removing the tumor from the top down, he can clearly see when he is reaching healthy tissue allowing him to stop before substantial collateral damage occurs. This is extremely desirable in brain and spine surgery, where tissue does not regenerate. Gastrointestinal surgeons have used the device as well for lesions of the liver and spleen, for the same reasons.

The required specifications, designs and engineering elements of such ultrasonic aspirators have become well known to the art in the intervening time. Although the technology is mature, several improvements can be made to enhance the ease of use and applicability to a wider range of procedures.

One side effect of any surgery is bleeding when the veins, arteries or capillaries are severed. Ultrasonic surgery is more sparing of blood vessels than knives because the collagen content of the vessels is more resistant to ultrasonic emulsion. However, the capillaries and small vessels will be compromised upon exposure to high amplitude ultrasonic tools. When these vessels are severed or punctured bleeding will of course occur. The surgeon will then be forced to pause the procedure, remove the ultrasonic tool from the site and generally reach for a cauterizing device of some type to close off the bleeder. Once coagulation has been achieved, then the surgeon can grab the ultrasonic tool, reposition it in the wound site and continue the removal of tissue. This situation repeats itself often in the course of the operation, lengthening the time of the procedure and coincidently the risk to the patient. It is therefore desired to find a way to cauterize tissue with the ultrasonic tool in place so the surgeon can stop bleeding with minimal downtime caused by switching tools and positions.

Several improvements to the basic design of the ultrasonic aspirator have been disclosed over the years which allows some degree of cauterization subsequent to or simultaneously with ultrasonic ablation. Most center on the application of RF cautery currents to the tool or probe itself. This has the effect of turning the ultrasonic tool into a monopolar RF cauterizer.

In a non-ultrasonic RF cauterizer, the tip of the tool is energized with a voltage sometimes exceeding 3000 volts RMS. The frequency of the voltage is very high, in order to prevent cardiac arrest in the patient. These frequencies are generally greater than 500,000 hertz. In monopolar RF, the tool is one pole of the electrical circuit. The second pole is generally a large piece of metal foil which the patient lays on during the procedure. The bare skin touching the foil makes an effective electrical contact. As the tool touches the tissue and the RF voltage is energized, a complete circuit path is created. The currents are very high, reaching 5 amps in some cases. At these currents, significant joule heating occurs in the tissue, raising the temperature higher than the burning temperature of 42° C. Continued operation dries the tissue by evaporating the water content. Cauterization then occurs. Since the back plate is very large in relation to the tool tip, the current "fans out" as it leaves the tool tip and thereby lowers the current density in the tissue to a point where the temperature rise in the tissue is reduced to that below burning. This minimizes collateral burning and tissue damage.

However, as large as the plate is, some collateral damage occurs away from the bleeder site. This collateral damage cannot be controlled reliably by the physician and is of great concern when operating on the brain. If the damage is two widespread, mental capacity or memory may be affected negatively. In addition, electrical current is forced to flow through viable tissue to the ground plate. Again, neurological damage may occur in some organs that are susceptible to damage due to this current, such as the brain, heart and nerve bundles. Other organs, such as the liver or spleen, are less susceptible to current effects.

Researchers have found a way to minimize or eliminate this current path by designing a tool that includes two electrical poles or contacts. This is called bipolar RF cauterization. Here the current flows between the two poles through the intervening tissue. No current path to the back is allowed. Therefore, the tissue that is damaged is only that caught between the two contacts, which can be very small.

Designers have found a way to add monopolar cautery to ultrasonic devices by connecting one electrical contact to the vibrating tip of the ultrasonic device. Several patents have disclosed concepts and techniques for this, such as U.S. Pat. No. 4,931,047 to Broadwin, et al. Here, the tip of the ultrasonic tool is the single pole that touches the tissue. The surgeon will generally stop ultrasonic vibration and turn on the cautery voltage. Current leaves the tip of the probe and goes through the body to the back plate. This has been shown to be effective in eliminating the need for switching tools to stop bleeding, saving time and effort on the doctor's part. However, all of the detriments of monopolar cautery still exist. Neurosurgeons are especially reticent to allow significant current to flow through brain or spinal cord tissue for fear of inducing neurological damage. In addition, the piezoelectric crystals of the ultrasonic transducer stack must be isolated from the cautery voltage or damage to the transducer or electronics will occur.

OBJECTS OF THE INVENTION

It is an object of the present invention to provide an ultrasonic treatment device or instrument having electrocautery capability.

Another object of the present invention is to provide such a device that eliminates the above-described deficiencies in conventional systems.

A further object of the present invention to provide such a device or instrument which is easy to use and which provides reliable cautery effects while minimizing patient risk during an ultrasonic aspiration procedure.

Yet another object of the present invention is to provide such a device or instruments with a capability of grasping and clamping tissue or vessels prior to and concurrent with electrocautery.

A related object of the present invention is to provide an associated method which combines ultrasonic ablation with electrocautery in a manner that is easy to use.

SUMMARY OF THE INVENTION

An ultrasonic medical treatment device pursuant to the present invention comprises a casing, an elongate probe, a transducer assembly, a sheath and a plurality of electrode members. The casing is generally in the form of a handpiece which facilitates manipulation by a surgeon. The probe is mounted to and extends from the casing and has an axis and a free end serving as an operative tip. The transducer assembly is mounted to the casing and is operatively connected to the probe for generating vibrations of at least one ultrasonic frequency in the probe. As is well known, the ultrasonic vibration frequency is a resonant frequency of the probe, whereby standing waves are produced in the probe. The sheath surrounds the probe. The electrode members are connectable to an RF voltage source and are mounted at least indirectly to the casing so as to permit relative motion between the electrode members and the probe.

In a preferred embodiment of the invention, the electrode members are attached to the sheath, which is movably mounted to the casing. It is also preferred that the electrode members are fixed to and substantially embedded in the sheath. The electrode members have exposed portions disposed proximately to the operative tip of the probe for forming electrically conductive contact with organic tissues at a surgical site in a patient.

More particularly, the sheath is movably mounted to the casing for reciprocatable motion along the axis of the probe, whereby the tip of the probe may be alternately covered and exposed. Thus, during an ultrasonic use of the instrument, the sheath is retracted to expose the operative tip of the probe, which is energized by a predetermined ultrasonic vibration produced by the transducer assembly. Should a blood vessel become severed by ultrasonic ablation, the action of the transducer assembly is interrupted and the sheath slid forward, in a distal direction, to cover the tip of the probe and to facilitate contact between the exposed portions of the electrode members and the region about the severed blood vessel. The electrode members are then connected to a radio-frequency current source to generate a current flow between the exposed portions of the electrode members.

The electrode members may be exactly two in number. In that case, the exposed portions of the electrode members are preferably disposed at an angle of less than 90° from one another. However, in some applications it may be preferred to have the exposed portions of the electrode members angularly spaced by a greater angle, up to 180°.

In another embodiment of the invention, there are two or more pairs of electrode members, with the members of each pair being disposed adjacent to one another along the circumference of the sheath. In this embodiment, a manually operable switching circuit may be operatively connected between the power source and the electrode members for determining which pair of electrode members is to be energized. The operating surgeon selects that pair of electrode members which is most closely located to a bleeding site.

Pursuant to another feature of the present invention, the electrode members are movable in parallel to the axis of the probe.

A medical surgical method in accordance with the present invention utilizes an ultrasonic medical treatment device having a casing and an elongate probe mounted to and extending from the casing, the probe having an axis and a free end serving as an operative tip, a transducer assembly mounted to the casing being operatively connected to the probe, a plurality of electrode members being mounted at least indirectly to the casing. The method comprises inserting a distal end portion of the probe into a patient, thereafter energizing the transducer assembly to generate a standing wave of an ultrasonic frequency in the probe, ablating tissues of the patient at the operative tip of the probe during the generating of said standing wave, connecting the electrode members to an RF voltage source, and cauterizing tissues in the patient owing to the conduction of current between exposed portions of the electrode members.

Pursuant to another feature of the present invention, the electrode members are moved relative to the probe, thereby placing the exposed portions of the electrode members in a predeterminable location relative to the operative tip. Where the electrode members are connected to a sheath, the moving of the electrode members may be accomplished by shifting the sheath relative to the probe.

In a further embodiment, the two electrodes may be spaced 180 degrees apart and be hinged nearer the proximal end of the sheath. Two protuberances may be provided, extending outside the outer sheath assembly, which contact the rigid metal electrodes. By sliding the sheath forward, the distal ends of the electrodes are exposed. These electrodes may be manipulated by the surgeon to allow tissue to fill the gap between said electrodes. By squeezing the protuberances, the surgeon may apply a pinching force on the tissue to help close severed vessels while applying electrocautery current.

It is to be noted that the electrodes may be used to ablate tissues of the patient in addition to cauterizing the ablated tissues.

BRIEF DESCRIPTION OF THE DRAWINGS

FIG. 1A is a partial longitudinal cross-section view of a n ultrasonic tissue ablation instrument with electrocautery, in accordance with the prior art.

FIG. 1B is a side elevational view of a transducer assembly used in the prior-art surgical instrument of FIG. 1A.

FIG. 2A is a schematic side-elevational view of a human subject, showing an electrocautery plate and, in phantom lines, a possible current path where the instrument of FIG. 1A is used in neurosurgery.

FIG. 2B is another schematic side-elevational view of a human subject, showing an electrocautery plate and, in phantom lines, another possible current path where the instrument of FIG. 1A is used in neurosurgery.

FIG. 3A is a partial longitudinal cross-sectional view of a distal end portion of an ultrasonic tissue ablation instrument with electrocautery, in accordance with the present invention.

FIG. 3B is an end elevational view of the instrument of FIG. 3A, taken from the right said in FIG. 3A.

FIG. 4A is a partial longitudinal cross-sectional view, taken along line IVA—IVA in FIG. 4B, of a distal end portion of another ultrasonic tissue ablation instrument with electrocautery, in accordance with the present invention.

FIG. 4B is an end elevational view of the instrument of FIG. 4A, taken from the right side in FIG. 4A.

FIG. 5A is a partial longitudinal cross-sectional view of the tissue ablation instrument of FIGS. 3A and 3B, depicting one structure for shifting a sheath and electrodes relative to an ultrasonic probe and showing the sheath in a retracted position to expose a free end of the probe.

FIG. 5B is a partial longitudinal cross-sectional view similar to FIG. 5A, showing the sheath in an extended position to cover a free end of the probe and place operative ends of the electrodes in contact with organic tissues at a surgical site.

FIG. 6A is a partial longitudinal cross-sectional view of the tissue ablation instrument of FIGS. 3A and 3B, depicting another structure for shifting the sheath and electrodes relative to the probe and showing the sheath in a retracted position to expose the free end of the probe.

FIG. 6B is a partial longitudinal cross-sectional view similar to FIG. 6A, showing the sheath in an extended position to cover a free end of the probe and place operative ends of the electrodes in contact with organic tissues at a surgical site.

FIG. 7A is a perspective view of a distal end portion of yet another ultrasonic tissue ablation instrument with electrocautery, in accordance with the present invention, showing a pair of electrodes hingedly mounted to a movable sheath disposed in a retracted position to expose an operating tip of an ultrasonic ablation probe.

FIG. 7B is a perspective view of the instrument of FIG. 7A, depicting the movable sheath slid forward to cover the operating tip of the ultrasonic ablation probe and to expose the distal ends of the electrodes.

DETAILED DESCRIPTION OF THE PREFERRED EMBODIMENTS OF THE INVENTION

Disclosed herein are various hardware configurations that will allow bipolar RF cautery to be used on organic tissues at a surgical site simultaneously with or immediately after ultrasonic ablation of tissue. The electrical connections are isolated from the ultrasonic tool thereby allowing the piezoelectric crystals to be floating with respect to this potential.

In the prior art, as shown in FIG. 1A, an ultrasonic probe 12 is connected one pole of an RF cauterizer (not shown) by a wire 14. Alternatively, an electrode member, conductive O rings or other methods known to the art (none shown) may be used. In the embodiment of FIGS. 1A and 1B, a front driver 16 of the transducer is also rendered live, which necessitates that the metal parts be insulated from the grip or handle 17 of the instrument. If the transducer assembly 18 is of the electrostrictive type with piezoelectric crystals 20, the crystals must be electrically isolated from the front driver 16 by methods known to the art such as using ceramic washers 22 and 24 as insulation in the crystal stack (FIG. 1B). A disadvantage of using isolators is that they generally reduce the electromechanical coupling efficiency, thereby leading to transducer heating and higher power requirements for a given output amplitude.

The other pole of the RF cauterizer is attached to a back plate 26 that contacts the patient's bare skin, as shown in FIGS. 2A and 2B. Then the entire body becomes part of the electrical connection. Possible current paths 28 and 30 are shown in FIGS. 2A and 2B.

As depicted in FIGS. 3A and 3B, both electrical poles or electrode members 32 and 34 of an electrocautery system are attached to and, more specifically, embedded in, a flexible silicone sheath 38 that surrounds an elongate ultrasonic probe 40. Ultrasonic aspirators require the addition of a sterile solution of saline into the wound site to irrigate the area and improve ablation. Sheath 38 serves to define, with probe 40, an annular conduit 42 for this saline solution.

In the embodiment of FIGS. 3A and 3B, electrode members 32 and 34 in the form of wires are molded into the silicone sheath or flue 38. The distal ends or tips 44 and 46 of the electrodes members 32 and 34 protrude from the distal end of sheath 38, forming two electrodes.

By utilizing the sheath 38 as a holder for the two electrode members 32 and 34 of the bipolar device, the electrical connections do not touch the tool itself. The close proximity of electrode members 32 and 34, and particularly exposed tips 44 and 46 thereof, allows a very short circuit path (FIG. 3B) for the cauterizing current. To use of the cauterizing capability of the instrument of FIGS. 3A and 3B, the instrument is rotated about a longitudinal axis 48 by the surgeon in order to approximate the exposed tips 44 and 46 of the electrode members 32 and 34 to bleeding tissues at a surgical site inside a patient.

FIGS. 4A and 4B depict an alternative configuration of electrodes 50–53 in a flexible silicone sheath 54 surrounding an ultrasonic probe 56. Electrodes 50–53 are circumferentially equispaced about the sheath 54. Electrodes 50–53 are ring segments (i.e., arcuate about an axis of sheath 54) molded into the end of sheath 54. Electrodes 50–53 have gaps between them for insulation purposes. Electrodes 50–53 are connected to electrode wires 58 and 60 that are embedded in sheath 54. The wires 58 and 60 are each connected to two electrodes or segments 50–53 disposed 180° apart. During an electrocautery operation, current is conducted between each pair of adjacent electrodes, thus producing four zones of possible tissue cauterization corresponding to the four gaps between electrodes 50–53.

In the embodiment of FIGS. 4A and 4B, a finer control of cauterization location may be achieved by having electrodes 50–53 connected to respective wires. Wires 58 and 60 are thus each connected to a single electrode 50, 51, 52, or 53. In this embodiment, a single pair of adjacent electrodes 50–53 is selected for energization at any one time. Generally, a pair is selected that is considered closest to bleeding tissues at a surgical site in a patient. When the RF current is energized, the segments will allow current to flow between the gaps of the segmented ring around the periphery of the sheath end. It can be envisioned by those schooled in the art that logic circuitry may be provided to energize only two segments of a multi-segmented ring to allow current to pass through only one or two gaps and not all of the gaps provided.

The configurations of FIGS. 3A, 3B and 4A, 4B have been developed to provide physicians with designs that can be used without losing dexterity or visibility of the operation site. The electrode member configurations of FIGS. 3A, 3B and 4A, 4B allow for bipolar cauterization without energizing the tool tip itself.

In order to allow the surgeon the best visualization of the operative field, mechanisms have been developed for use with the devices of FIGS. 3A, 3B and 4A, 4B that provide for a longitudinal translation of sheaths 38 and 54 alternately in a distal direction and a proximal direction. While the ultrasound is active, sheath 38 or 54 is slid back to expose the distal end or operative tip 78 or 79 of the probe 40 or 56. When RF cautery is needed, the surgeon uses one finger (e.g., a thumb) to slide the sheath 38 or 54 forward to place the electrodes 44, 46 or 50–53 in contact with the tissue. FIGS. 5A and 5B show a first embodiment of this mechanism, constructed of molded or machined plastic, while FIGS. 6A and 6B show an alternative embodiment of the slide mechanism. Although FIGS. 5A, 5B, 6A, and 6B depict the electrode configuration of FIGS. 3A and 3B, it is to be understood that the electrode configuration of FIGS. 4A and 4B could be used instead.

As illustrated in FIGS. 5A and 5B, probe 40 is connected at a proximal end to a piezoelectric transducer assembly 62, while sheath 38 is affixed to the distal end of a polymeric inner tubular member 64 telescopingly cooperating with an outer tubular member or casing 66. Casing 66 extends in a rearward or proximal direction to form a handgrip or handpiece for a surgeon or other user of the ultrasonic/electrocautery instrument. Annular conduit 42 communicates at a proximal end with an annular passageway 68 formed by probe 40 and inner tubular member 64. Passageway 68 communicates with a saline source (not shown) via a nippled coupling 70 and an aperture 72 formed in inner tubular member 64. Inner tubular member 64 is provided with a projection 76 serving as a manually operable control knob for sliding sheath 38 and electrode members 32 and 34 (a) in the distal direction prior to the energization of electrode members 32 and 34 and electrode tips 44 and 46 in an electrocautery operation and (b) in a proximal direction prior to an ultrasonic ablation procedure in which probe 40 is vibrated by transducer assembly 62. During an ultrasonic ablation procedure, a free end or operative tip 78 of probe 40 vibrates with a maximized displacement (at an antinode of the standing wave generated in probe 40).

The telescoping cooperation of inner tubular member 64 and casing 66 enables a reciprocating motion of sheath 38 and electrode members 32 and 34 along the axis 48 of probe 40, whereby the operative tip 78 of the probe may be alternately covered and exposed. Thus, during an ultrasonic use of the instrument, sheath 38 is retracted to expose the operative tip 78 of the probe 40, which is energized by a predetermined ultrasonic vibration produced by the transducer assembly 62. Should a blood vessel become severed by ultrasonic ablation, the action of transducer assembly 62 is interrupted and sheath 38 is slid forward, in a distal direction, to cover tip 78 of probe 40 and to facilitate contact between the exposed portions of the electrode members, i.e. electrode tips 44 and 46, and the region about the severed blood vessel. Electrode members 32 and 34 are then connected to a radio-frequency current source (not illustrated) to generate a current flow between the exposed portions of the electrode members 32 and 34.

As depicted in FIGS. 6A and 6B, probe 40 is connected at a proximal end to a piezoelectric transducer assembly 80, while sheath 38 is affixed to the distal end of a polymeric tubular member 82 attached via an annular bellows 84 to a handpiece casing 86. Annular conduit 42 communicates at a proximal end with an annular passageway 88 formed by probe 40 and tubular member 82. Passageway 88 communicates with a saline source (not shown) via a nippled coupling 90 and an aperture 92 formed in tubular member 82. Tubular member 82 is provided with a projection 96 serving as a manually operable control knob for sliding sheath 38 and electrode members 32 and 34 (a) in the distal direction prior to the energization of electrode members 32 and 34 and electrode tips 44 and 46 in an electrocautery operation and (b) in a proximal direction prior to an ultrasonic ablation procedure in which probe 40 is vibrated by transducer assembly 62.

The distensible connection of tubular member 82 and casing 86 via bellows 84 enables a reciprocating motion of sheath 38 and electrode members 32 and 34 along the axis 48 of probe 40, whereby the operative tip 78 of the probe may be alternately covered and exposed, as discussed hereinabove with reference to FIGS. 5A and 5B. Bellows 84 provides the mechanism with a seal against the transducer housing (tubular member 82) to prevent fluid leaks.

As illustrated in FIGS. 7A and 7B, two electrodes 102 and 104 may be spaced 180° apart and hinged (e.g., via a flexible joint) nearer the proximal end of a sheath 106. Sheath 106 is provided with two pairs of longitudinal parallel slots 108 defining respective fingers 110 and 112 in which electrode wires (not separately illustrated) are embedded. Two actuators in the form of protuberances 114 and 116 are provided, extending through respective opposed apertures 118 (only one shown) in a casing 120. Protuberances 114 and 116 are connected to fingers 110 and 112, respectively, near the proximal ends thereof. Pushing one or both protuberances 114 and 116 in a longitudinal direction, along an axis (not indicated) of the instrument, slides sheath 106 either forward to cover an operating tip of an ultrasonic probe 122, as depicted in FIG. 7B, or rearwards to expose the probe tip, as depicted in FIG. 7A. A surgeon may also manipulate electrodes 102 and 104 to insert target organic tissues between the electrodes prior to an electrocautery operation. By squeezing protuberances 114 and 116 towards one another, the surgeon may apply a pinching force on the tissue to help close severed vessels while applying electrocautery current via electrodes 102 and 104. In an application of compressive pressure to protuberances 114 and 116 electrodes 102 and 104 function as tweezers, exerting a squeezing force on trapped tissue, thereby enhancing the vessel sealing effect of the electrodes and minimizing collateral damage.

Although the invention has been described in terms of particular embodiments and applications, one of ordinary skill in the art, in light of this teaching, can generate additional embodiments and modifications without departing from the spirit of or exceeding the scope of the claimed invention. It is to be noted, for instance, that the electrocatuery portion of a combined ultrasonic ablation and electrocautery tool as disclosed herein may be used for ablation, as well as cautery. It is to be noted, in addition, that the electrodes may be attached to the probe casing or frame by means other than the sheath. Accordingly, it is to be understood that the drawings and descriptions herein are proffered by way of example to facilitate comprehension of the invention and should not be construed to limit the scope thereof.

What is claimed is:

1. An ultrasonic medical treatment device comprising:
    a casing;
    an elongate probe mounted to and extending from said casing, said probe having an axis and a free end serving as an operative tip;
    a transducer assembly mounted to said casing and operatively connected to said probe for generating vibrations of at least one ultrasonic frequency in said probe;
    a sheath surrounding said probe; and
    a plurality of electrode members attached to said sheath, said electrode members being connectable to an RF voltage source, at least one of said electrode members being movable in a transverse direction relative to said axis.

2. The medical treatment device defined in claim 1 wherein said sheath is movably mounted to said casing for reciprocatable motion along said axis of said probe, whereby said tip of said probe may be alternately covered and exposed.

3. The medical treatment device defined in claim 2 wherein said electrode members are fixed to said sheath.

4. The medical treatment device defined in claim 3 wherein said electrode members are substantially embedded in said sheath and have exposed tips proximate to said operative tip of said probe.

5. The medical treatment device defined in claim 4 wherein said electrode members are exactly two in number.

6. The medical treatment device defined in claim 4 wherein said electrode members include a plurality of pairs of electrode members.

7. The medical treatment device defined in claim 2 wherein said at least one of said electrode members is hingedly secured to said sheath, further comprising at least one actuator operatively connected to said one of said electrode members for pivoting said one of said electrode members towards the other of said electrode members.

8. The medical treatment device defined in claim 7 wherein said sheath is formed with at least one pair of parallel slots defining a hinged finger, said one of said electrode members being mounted to said hinged finger.

9. The medical treatment device defined in claim 8 wherein said one of said electrode members is at least partially embedded in said finger.

10. The medical treatment device defined in claim 7 wherein said actuator is a protuberance manually engageable to slide said sheath alternately in a proximal and a distal direction.

11. The medical treatment device defined in claim 1 wherein said electrode members are mounted to said sheath so as to be movable in an axial direction relative to said probe.

12. The medical treatment device defined in claim 1 wherein said electrode members are fixed to said sheath.

13. The medical treatment device defined in claim 1 wherein said electrode members are substantially embedded in said sheath and have exposed tips proximate to said operative tip of said probe.

14. An ultrasonic medical treatment device comprising:
    a casing;
    an elongate probe mounted to and extending from said casing, said probe having an axis and a free end serving as an operative tip;
    a transducer assembly mounted to said casing and operatively connected to said probe for generating vibrations of at least one ultrasonic frequency in said probe;
    a sheath surrounding said probe; and
    a plurality of electrode members connectable to an RF voltage source, said electrode members being mounted at least indirectly to said casing so as to permit relative motion between said electrode members in a direction transverse to said axis.

15. The medical treatment device defined in claim 14, further comprising means mounting said electrode members to said casing so as to permit relative motion between said electrode members and said probe.

16. The medical treatment device defined in claim 15 wherein said means mounting said electrode members to said casing includes said sheath, said sheath being movably mounted to said casing for reciprocatable motion along said axis of said probe, whereby said tip of said probe may be alternately covered and exposed.

17. The medical treatment device defined in claim 16 wherein said electrode members are mounted to said sheath so as to permit a transverse motion of a distal end of at least one said electrode members relative to said probe, thereby permitting an adjustment in the distance between the distal ends of said electrode members.

18. The medical treatment device defined in claim 17 wherein at least one of said electrode members is hingedly secured to said sheath, further comprising at least one actuator operatively connected to said one of said electrode members for pivoting said one of said electrode members towards the other of said electrode members.

19. The medical treatment device defined in claim 18 wherein said sheath is formed with a plurality of pairs of parallel slots defining respective hinged fingers, said electrode members being mounted to respective ones of said hinged fingers.

20. The medical treatment device defined in claim 19 wherein said electrode members are at least partially embedded in said fingers.

21. The medical treatment device defined in claim 18 wherein said actuator is a protuberance manually engageable to slide said sheath alternately in a proximal and a distal direction.

22. The medical treatment device defined in claim 16 wherein said electrode members are substantially embedded in said sheath and have exposed tips proximate to said operative tip of said probe.

23. A method for conducting a medical surgical procedure, comprising:
    providing an ultrasonic medical treatment device having a casing and an elongate probe mounted to and extending from said casing, said probe having an axis and a free end serving as an operative tip, a transducer assembly mounted to said casing being operatively connected to said probe, a plurality of electrode members being mounted at least indirectly to said casing;
    inserting a distal end portion of said probe into a patient;
    thereafter energizing said transducer assembly to generate a standing wave in said probe, said standing wave having a wavelength corresponding to an ultrasonic frequency;
    during the energizing of said transducer assembly, ablating tissues of the patient at said operative tip of said probe;
    connecting said electrode members to an RF voltage source;
    moving said electrode members relatively towards one another, in a direction transverse to said axis; and
    thereafter cauterizing tissues in the patient owing to the conduction of current between exposed portions of said electrode members.

24. The method defined in claim 23, further comprising moving said electrode members relative to said probe, thereby placing the exposed portions of said electrode members in a predeterminable location relative to said operative tip.

25. The method defined in claim 24 wherein said electrode members are attached to said sheath, the moving of said electrode members relative to said probe including moving said sheath relative to said probe.

26. The method defined in claim 25 wherein the moving of said electrode members relative to said probe includes translating said sheath in parallel to said probe.

27. The method defined in claim 23 wherein the moving of said electrode members relatively towards one another includes moving at least one of said electrode members in a transverse direction relative to said probe and relative to another of said electrode members, thereby changing a distance between exposed portions of said one of said electrode members and said another of said electrode members.

28. The method defined in claim 23, further comprising using said electrode members to ablate tissues of the patient.

* * * * *